US006142153A

United States Patent [19]

Monroe

[11] Patent Number: 6,142,153

[45] Date of Patent: Nov. 7, 2000

[54] STEREOTAXIC HEADFRAME DRAPE

[76] Inventor: Savola Monroe, 4970 Mahonia Dr., Charlottesville, Va. 22911

[21] Appl. No.: 09/260,888

[22] Filed: Mar. 2, 1999

Related U.S. Application Data

[60] Provisional application No. 60/076,507, Mar. 2, 1998.

[51] Int. Cl.[7] .................... A61B 19/00

[52] U.S. Cl. .................... 128/849; 128/857

[58] Field of Search .................... 128/849–856, 128/848, 857; 602/18

[56] References Cited

U.S. PATENT DOCUMENTS

| | | | |
|---|---|---|---|
| 4,457,026 | 7/1984 | Morris | 128/851 |
| 4,644,944 | 2/1987 | MacConkey | 128/849 |
| 5,031,609 | 7/1991 | Fye | 128/857 |
| 5,787,894 | 8/1998 | Holt | 128/848 |
| 5,893,365 | 4/1999 | Anderson | 602/17 |

*Primary Examiner*—Michael A. Brown
*Attorney, Agent, or Firm*—Sheldon H. Parker

[57] ABSTRACT

A headframe drape for use during stereotaxic procedures, and a method for using the same, is described. The drape is designed to be inexpensive and easy to use. The drape comprises a single rectangular body having first and second connection portions on either side thereof, the first connection portion having hook material thereon and the second connection portion having loop material thereon. The first and second connection portions may be secured together using the hook and loop material, so that a headframe, base ring, or both a headframe and base ring may be secured and adjusted to any desirable degree during a stereotaxic procedure. The drape may be placed at the crown of a patient's head and draped down over the patient's ears, at which point a base ring or headframe, or both, may be placed over the patient's head, and the first and second connection portions secured together using the hook and loop material in order to adjust and secure the base ring or headframe, or both, in a position relative to the patient's head.

17 Claims, 4 Drawing Sheets

10

16

12

STEREOTAXIC HEADFRAME DRAPE

CROSS-REFERENCE TO RELATED PROVISIONAL APPLICATION

The present patent application claims the benefit of the earlier filing date of pending U.S. Provisional Patent Application Ser. No. 60/076,507, filed Mar. 2, 1998, which is incorporated by reference herein in its entirety.

BACKGROUND OF THE INVENTION

1. Field of the Invention

The invention discloses a inexpensive, easy to use, headframe drape for use during stereotaxic procedures.

2. Brief Description of the Prior Art

Stereotaxic procedures, which are now done world-wide, require that a frame be positioned around the heads of patients prior to three-dimensional imaging or other procedures. Drapes are used to support these head frames while they are being applied to the patient. Although drapes are a marked improvement over the painful alternative method of attaching the frame to special ear plugs during positioning, current available drapes have several serious shortcomings.

First, frame drapes are not designed to fit all frames. In some cases two drapes must be combined, which increases the time and complexity of the positioning. Second, drapes are of cloth and must be laundered after each use. This process takes staff time and effort, and turn-around time is dependent on general hospital facilities. Moreover, these drapes must be tracked to ensure sterile condition before re-use.

The disclosed drape is appropriate for all stereotaxic frame placements, so that only one is needed per procedure and positioning can be performed with improved speed and efficiency. Importantly, the disclosed drape is disposable, costs less than cloth drapes and eliminates laundry and sterility problems and costs.

SUMMARY OF THE INVENTION

A rectangular drape is disclosed for use with stereotaxic headframes which allows for easy adjustability of the headframe. The drape is provided with hook and loop material on opposing ends to allow the hook and loop to be secured at the top of the patient's head. The drape is placed over the patient's head and the headframe then placed on the patient's head, over the drape. The ends of the drape are lifted, and secured, at the top of the patient's head, thereby lifting the headframe and suspending the headframe off the patient's head. The use of the drape allow the distance between the headframe and the patient's head to be infinitely adjusted, providing an accurate reference point for the operator.

BRIEF DESCRIPTION OF THE DRAWINGS

The advantages of the instant disclosure will become more apparent when read with the specification and the drawings, wherein.

DETAILED DESCRIPTION OF THE INVENTION

With the increased number of gamma knives in use, an inexpensive, easy to use method of positioning and adjusting the headframe use during the procedure is preferable.

Figure 1:
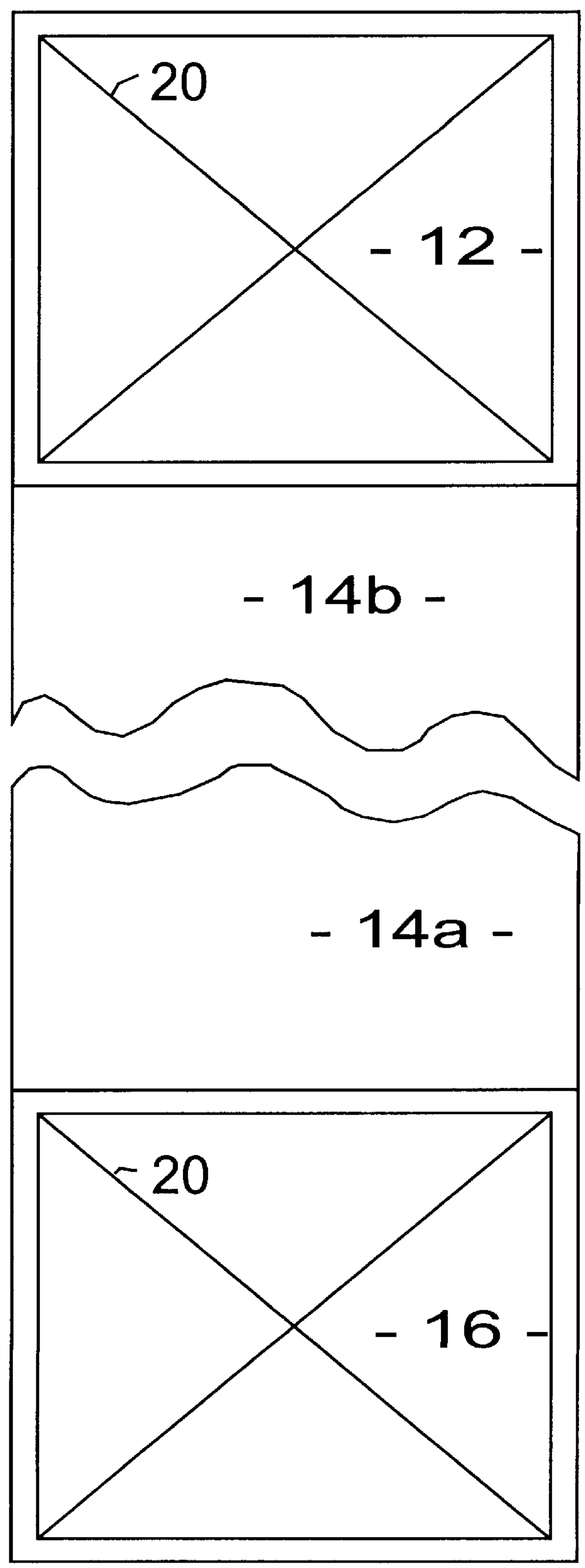
FIG. 1 is a fragmented top view of the disclosed drape.

The disclosed drape is used to position, vertically, the headframe without any discomfort to the patient. The drape 10, as illustrated in FIG. 1, is a length of paper material 14 having hook and wool material 12 and 16 at either opposing end. In the preferred embodiment, the dimensions, unfolded, are approximately 38 inches by 4 inches. The paper material 14 is preferably lightweight, compact for storage and tear resistant and have the ability to be sterilized. The preferred paper material 14 is known in the medical field as sterilization wrap and is used for a number of applications where sterility is required. The drape 10 as illustrated, has been segmented, showing both sides, 14*a* and 14*b*, of the body 14. As can be seen hereinafter, the hook and loop material 12 and 16 are on opposing sides of the body 14 to allow for the material to be secured. If the drape 10 is intended for universal use with various sized headframes, the hook and wool material 12 and 16 preferably have a length of approximately seven inches. This allows for an overlap sufficient to secure the drape 10 when used with the maximum sized headframe. In instances where the drape is being manufactured to work with one specific head frame, the length of the paper 14 as well as the hook and wool 12 and 16, can be specifically sized. A drape having the foregoing dimensions, is easily folded into a 7 inch by 4 inch unit which has a thickness of approximately 0.25 of an inch and weights less than 1.5 ounces. This compact size allows for easy storage and handling.

To manufacture the drape 10, sufficient layers of paper, or other material, are cut to the desired dimensions and layered to form the body 14. The number of layers will be dependent upon the weight of the material and will be obvious to those skilled in the art. If two or more layers are used, it may be preferably to stitch, or otherwise secure, the layers together prior to the addition of the hook material 12 and loop material 16. The hook and loop material 12 and 16 must be firmly secured to the body 14 in order to have the ability to withstand repeated separation and reaffixing. Additionally, since the weight-of the head frame 22 is supported by the hook and loop material 12 and 16, the method of securing the hook and loop material 12 and 16 to the body 14 must be sufficient to support the headframe 22 weight. The illustrated embodiment is stitched at perimeter line 18 to prevent the two sheets 14*a* and 14*b* from separating. The hook material 12 and wool material 16, are stitch not only around their perimeter but in a X at stitch lines 20. Alternative securing methods, such as hot melt glue, can be used dependent upon the materials of manufacture.

Figure 3:
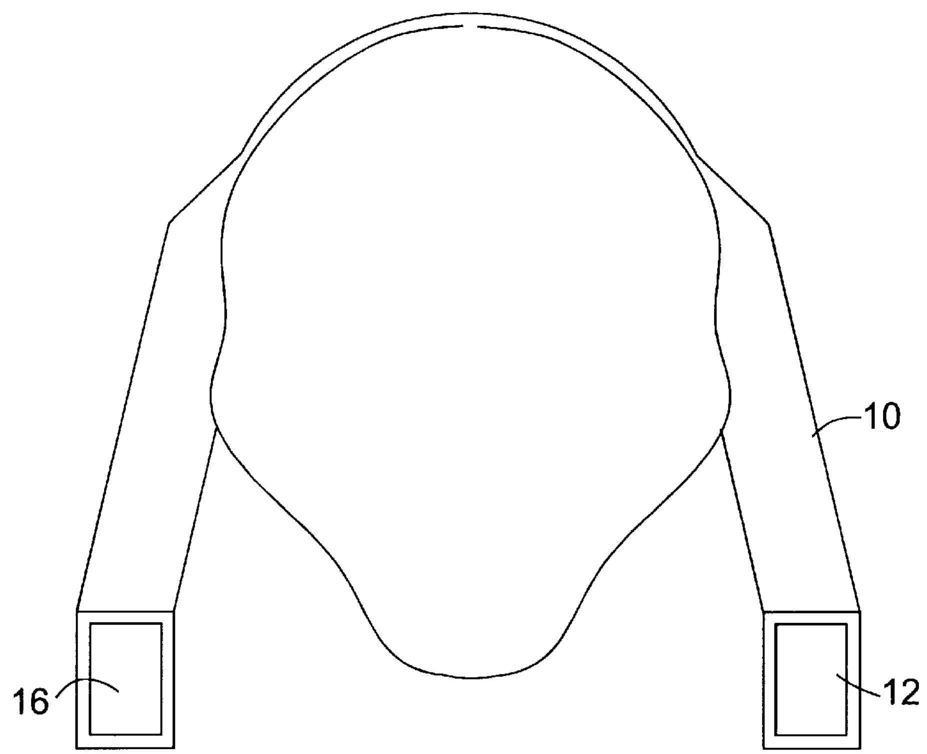
FIG. 3 is a front view of the drape placed over the patient's head.
Figure 2:
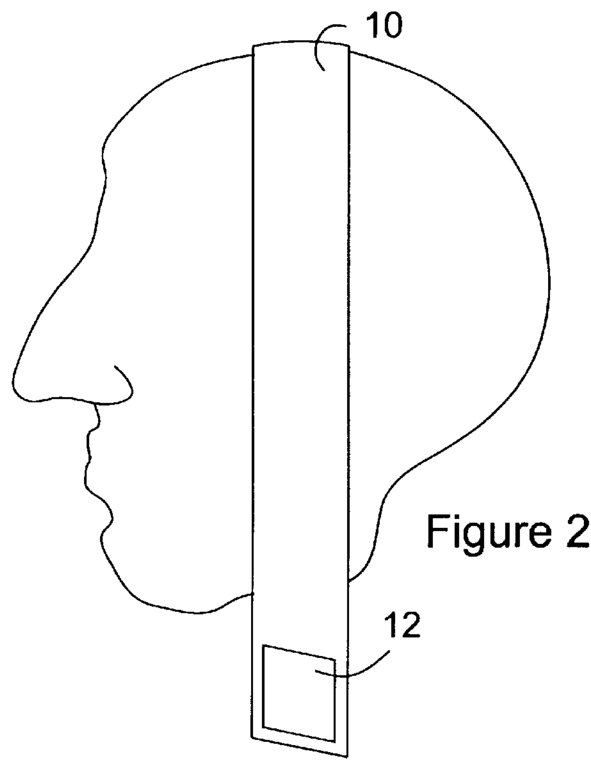
FIG. 2 is a side view of the drape placed over the patient's head in the initial position.
Figure 4:
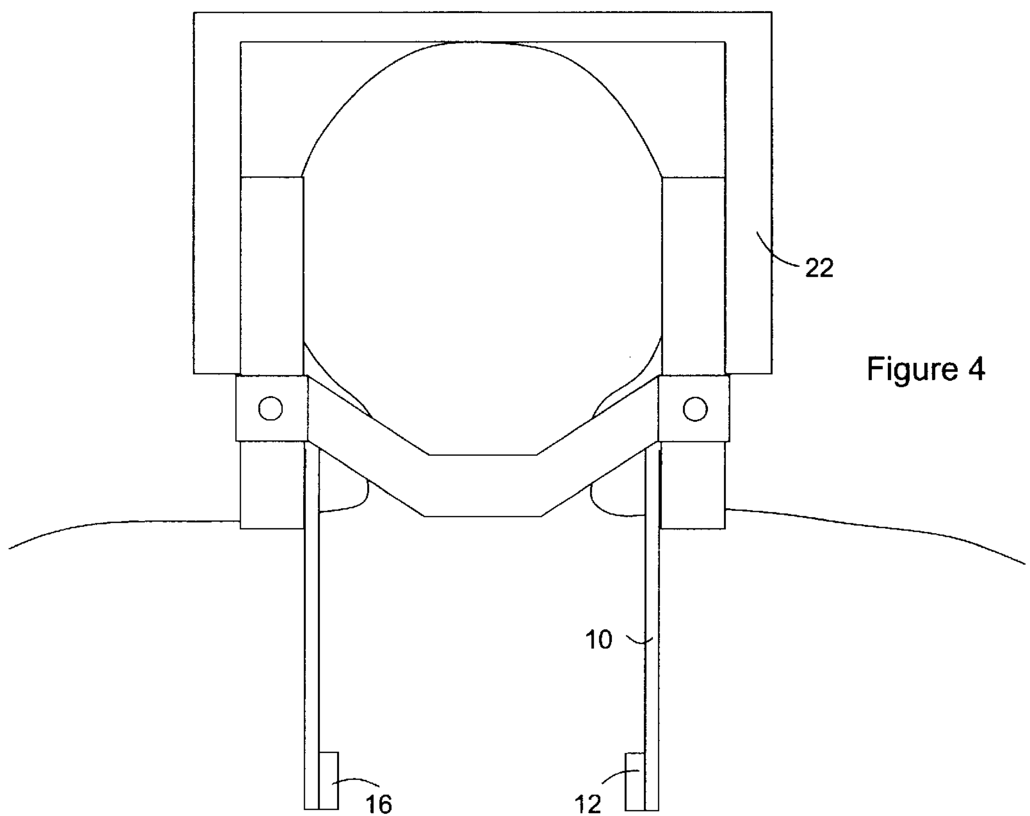
FIG. 4 is a front view of the head frame placed over the patient's head with the drape unattached.

To use the drape 10, the drape 10 unfolded and draped across the patient's head as illustrated in FIGS. 2 and 3. As can be seen in FIG. 2, the drape 10 is placed at the crown of the patient's head, draping down over the patient's ears. As can be seen in FIG. 4, the hook material 12 and loop material 16 are positioned on the drape body 14 to allow for contact with one another. Once the drape 10 is in position, the headframe 22 is placed over the patient's head. The headframe 22 is allowed to rest on the patient's head at this point, thereby allowing one person to perform the head frame adjustments simply by affixing the hook material 12 and loop material 16 to one another.

Figure 5:
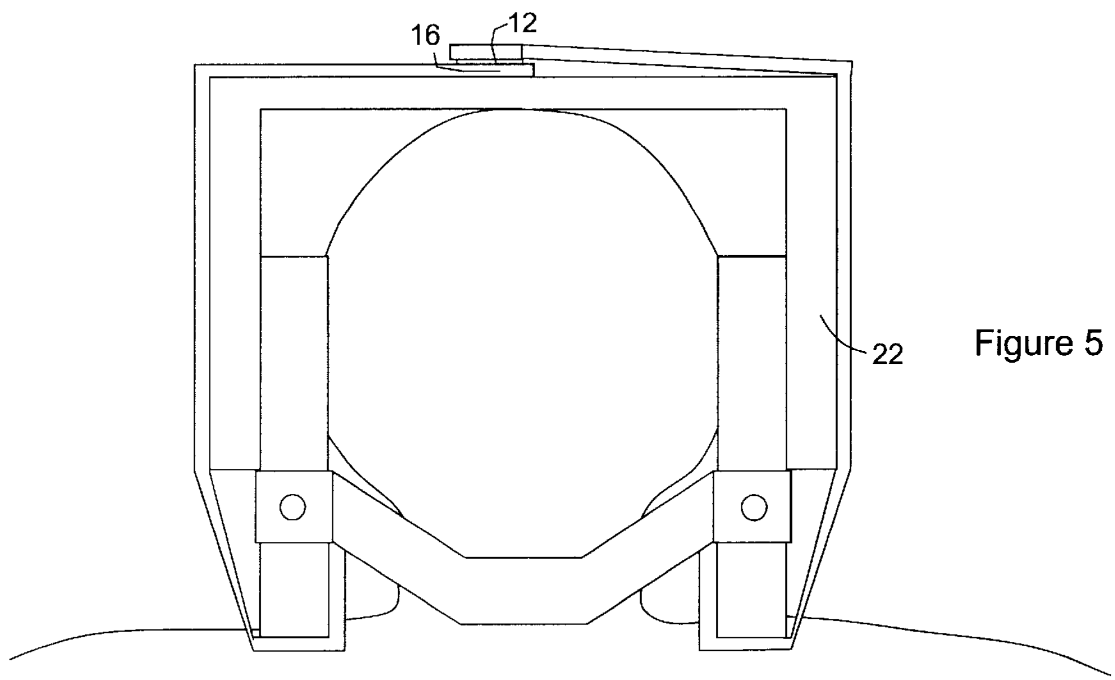
FIG. 5 is a front view of the drape attached securing the frame.
Figure 6:
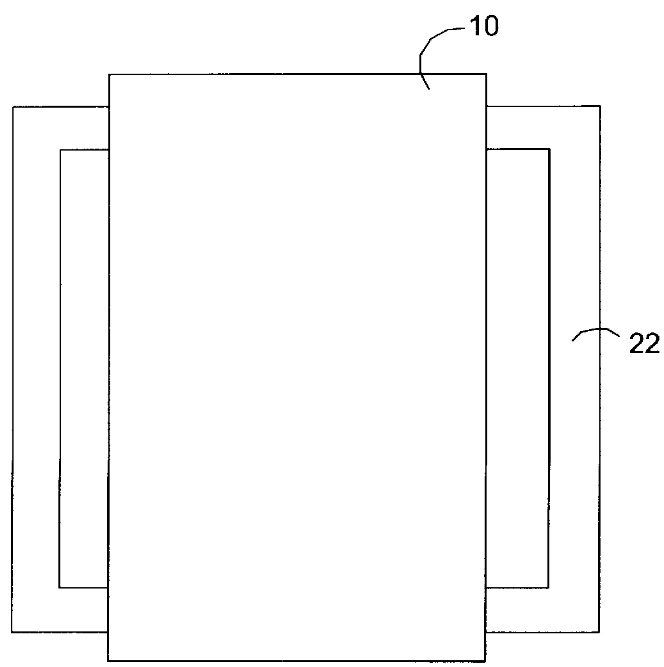
FIG. 6 is a side view of the secured drape.

Once the headframe 22 is positioned on the patient's head, the drape 10 is brought up on either side of the frame, as illustrated in FIGS. 5 and 6, and the hook and wool material 12 and 16 secured to one another. The use of the hook and wool material 12 and 16 allows the length, and therefore the distance between the headframe 22 and the patient's head, to be easily adjusted.

The headframe 22 serves as a reference point as to the location of the lesion. The headframe 22 must, therefore, have the ability to be infinitely adjusted in order to provide for accurate placement. Once the surgeon has specified the location of the lesion, the headframe 22 is positioned accordingly, providing the operator with the ability to direct the equipment as the appropriate area.

Figure 7:
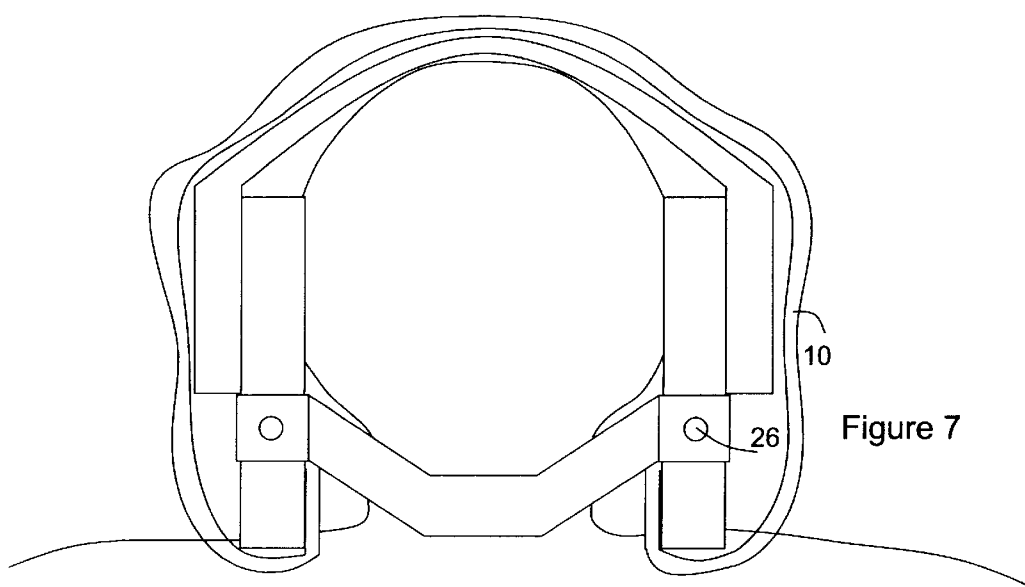
FIG. 7 is a front view of the drape used in conjunction with the base ring.

In some instances, however, the headframe is not necessary and only the base ring is used. FIG. 7 illustrates the disclosed drape 10 used with the base ring 26 without the addition of the headframe.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A drape for maintaining a Stereotaxic headframe in a predetermined position relative to a patient's head, said drape comprising:

a substantially rectangular body, said body having a width and a length and being substantially tear and stretch resistant, a first portion of said body to be placed adjacent the crown of the patient's head, and a second and third portion of said body lying along the side of the patient's head between the patient's head and the apparatus;

a first connection portion, said first connection portion having hook material and being affixed to a first surface of said body;

a second connection portion, said second connection portion having hook material and being affixed to a second surface of said body and in cooperative engagement with said first connection portion, wherein said drape has a weight of less than about 1.5 ounces and said first connection portion and said second connection portion are configured to be secured to one another at multiple positions, thereby enabling adjustment said length of said body to vary the relative position between the apparatus and the patient's head.

2. A drape as in claim 1, wherein said drape is disposable.

3. A drape as in claim 1, wherein said drape is folded into an approximately about 7 inch by 4 inch unit having a thickness of approximately about 0.25 inches for packaging and shipping.

4. A drape as in claim 1, wherein said drape is made of a lightweight material.

5. A drape as in claim 4, wherein said drape is made of paper.

6. A drape as in claim 5, wherein said drape is made of sterilization wrap.

7. A drape as in claim 4, wherein said drape may be folded into an approximately about 7 inch by 4 inch unit having a weight of less than approximately about 1.5 ounces.

8. A drape as in claim 4, wherein said drape is made of at least two layers of material.

9. A drape as in claim 8, wherein said at least two layers are secured by stitching along said drape perimeter.

10. A drape as in claim 8, wherein said drape is secured by stitching configured generally in an X pattern on said first connection end and said connection end of said drape.

11. A drape as in claim 8, wherein said at least two layers are secured by hot glue.

12. The drape of claim 1 wherein said first connection portion and said second portion are hook and loop material.

13. The drape of claim 1 wherein said length is determined by the size of the apparatus.

14. The drape of claim 1 wherein said length is approximately 38 inches and said width is approximately 4 inches.

15. A method of using a drape to secure an apparatus used in stereotaxic procedures in a predetermined position, said drape comprising a body, a first connection portion and a second connection portion, said first connection portion and said second connection portion being adjustable relative to one another, comprising the steps of:

a portion of said drape over the crown of a patient's head and draping the remaining portion said drape down over the patient's head;

placing a base ring adjacent the patient's head and over said drape;

bringing said first connection portion and said second connection portion proximate one another by wrapping said drape around the base ring to suspend the base ring within said drape;

overlapping said first connection portion and said second connection portion until base ring is in a predetermined position relative to the patient's head;

affixing said first connection portion of said drape to said second connection portion of said drape to secure the base ring in said predetermined position relative to the patient's head.

16. A method as in claim 15, further comprising a step of placing a headframe over the patient's head after placing a base ring adjacent the patient's head and before, so that said base ring and said headframe will be secured in a position relative to said patient's head.

17. A method as in claim 15, wherein said first connection portion and said second connection portion are hook and loop material configured for cooperative engagement for securing said first connection portion to said second connection portion, and wherein said position of said headframe relative to said patient's head is adjusted using said hook material and loop material.

* * * * *